United States Patent
Folan et al.

(10) Patent No.: US 11,026,818 B2
(45) Date of Patent: Jun. 8, 2021

(54) STENT WITH SELECTIVELY COVERED REGION

(71) Applicant: BOSTON SCIENTIFIC SCIMED, INC., Maple Grove, MN (US)

(72) Inventors: Martyn G. Folan, Galway (IE); Martin Burke, Galway (IE); Gerard Duignan, Roscommon (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 130 days.

(21) Appl. No.: 16/391,017

(22) Filed: Apr. 22, 2019

(65) Prior Publication Data

US 2019/0321204 A1    Oct. 24, 2019

Related U.S. Application Data

(60) Provisional application No. 62/661,431, filed on Apr. 23, 2018.

(51) Int. Cl.
| | | |
|---|---|---|
| *A61F 2/90* | (2013.01) | |
| *A61F 2/915* | (2013.01) | |
| *A61F 2/848* | (2013.01) | |
| *A61L 31/14* | (2006.01) | |

(52) U.S. Cl.
CPC .............. *A61F 2/915* (2013.01); *A61F 2/848* (2013.01); *A61F 2002/9155* (2013.01); *A61L 31/148* (2013.01)

(58) Field of Classification Search
CPC ........ A61F 2/915; A61F 2/878; A61F 2/2418; A61F 2/2415; A61F 2/2439
USPC .................................................. 623/2.1–2.19
See application file for complete search history.

(56) References Cited

U.S. PATENT DOCUMENTS

| | | | |
|---|---|---|---|
| 5,662,713 A | * | 9/1997 | Andersen .................. A61F 2/90 128/898 |
| 6,626,934 B2 | | 9/2003 | Blaeser et al. |
| 7,354,455 B2 | | 4/2008 | Stinson |
| 8,506,516 B2 | | 8/2013 | Kassab et al. |
| 8,753,407 B2 | | 6/2014 | Nguyen |
| 8,784,473 B2 | | 7/2014 | Tupil et al. |
| 8,801,647 B2 | | 8/2014 | Melanson et al. |
| 9,402,755 B2 | | 8/2016 | Norris et al. |

(Continued)

FOREIGN PATENT DOCUMENTS

WO    2018045795 A1    3/2018

OTHER PUBLICATIONS

International Search Report and Written Opinion dated Jul. 17, 2019 for International Application No. PCT/US2019/028569.

*Primary Examiner* — Suzette J Gherbi
(74) *Attorney, Agent, or Firm* — Seager, Tufte & Wickhem, LLP

(57) ABSTRACT

A stent with a selectively covered end region. The stent includes a radially expandable tubular framework and a covering surrounding the tubular framework. The covering includes a skirt surrounding a distal end region of the tubular framework which is selectively removable from the distal end region of the tubular framework to expose the distal end region of the tubular framework to permit hyperplastic tissue ingrowth through the distal end region of the tubular framework. For example, the skirt may be folded, rolled, collapsed, or separated from the remainder of the covering to expose the distal end region of the tubular framework.

17 Claims, 17 Drawing Sheets

(56) References Cited

U.S. PATENT DOCUMENTS

| | | |
|---|---|---|
| 9,439,790 B2 | 9/2016 | Clerc et al. |
| 9,579,186 B2 | 2/2017 | Hingston et al. |
| 9,763,819 B1 | 9/2017 | Sondreaal |
| 9,801,749 B2 | 10/2017 | Hingston et al. |
| 10,299,919 B2* | 5/2019 | Alkhatib ............... A61F 2/2418 |
| 10,426,592 B2* | 10/2019 | Folan ...................... A61F 2/90 |
| 2005/0080491 A1 | 4/2005 | Levine et al. |
| 2007/0219619 A1 | 9/2007 | Dieck et al. |
| 2009/0012544 A1 | 1/2009 | Thompson et al. |
| 2010/0256775 A1 | 10/2010 | Belhe et al. |
| 2011/0307070 A1 | 12/2011 | Clerc et al. |
| 2013/0138219 A1 | 5/2013 | Toomey et al. |
| 2014/0364959 A1 | 12/2014 | Attar et al. |
| 2016/0058545 A1 | 3/2016 | Toomey et al. |
| 2016/0058585 A1 | 3/2016 | Seddon et al. |
| 2016/0206449 A1 | 7/2016 | Mort et al. |
| 2017/0290653 A1* | 10/2017 | Folan ....................... A61F 2/04 |
| 2017/0325983 A1 | 11/2017 | Valdes et al. |
| 2019/0125517 A1* | 5/2019 | Cully .................. A61M 27/002 |
| 2019/0175327 A1 | 6/2019 | Xiao et al. |
| 2020/0289261 A1* | 9/2020 | Qi ........................ A61F 2/2433 |

* cited by examiner

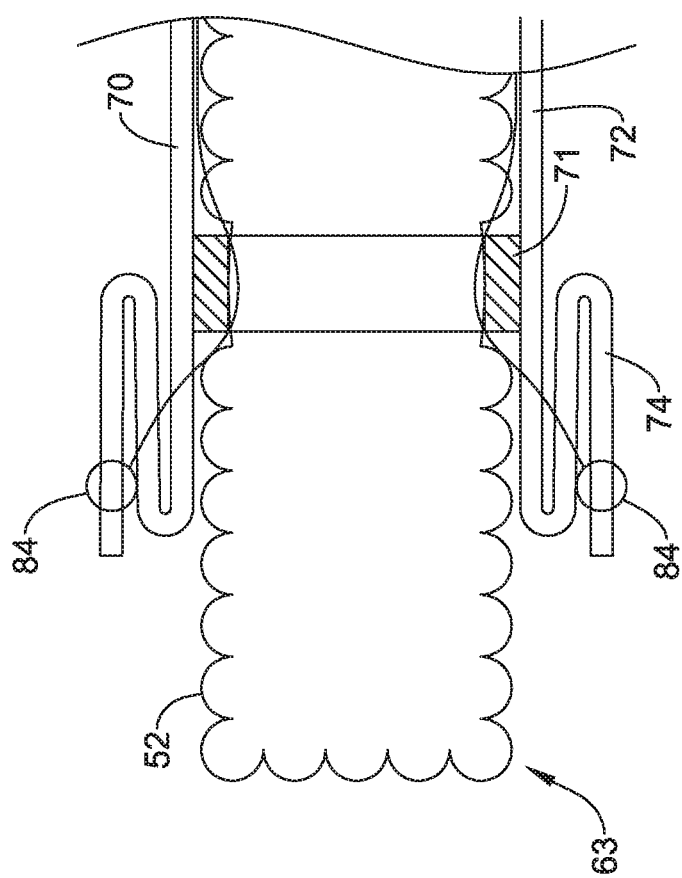

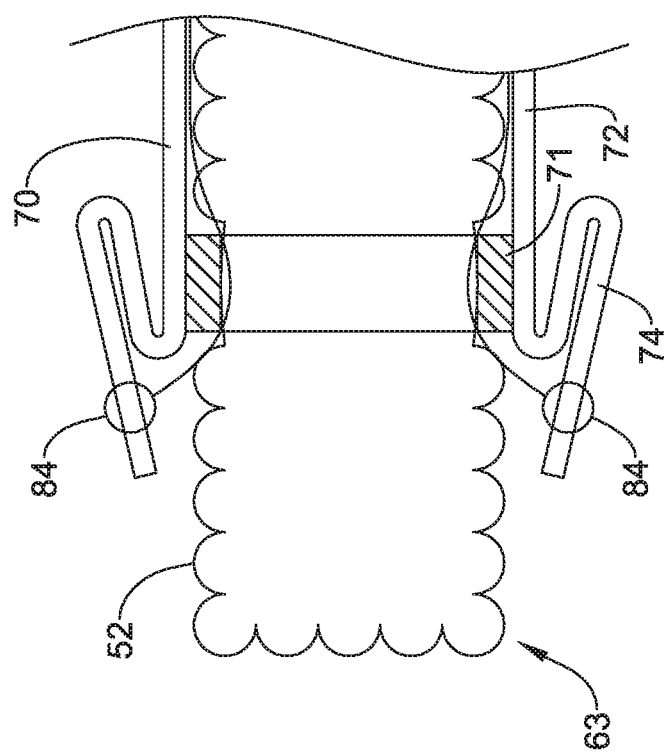

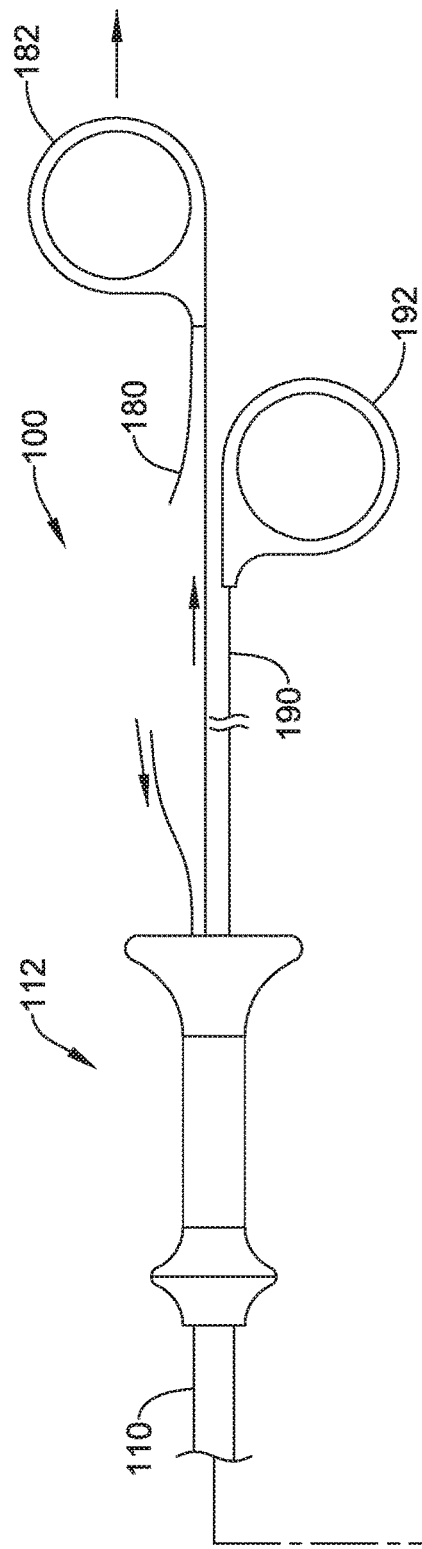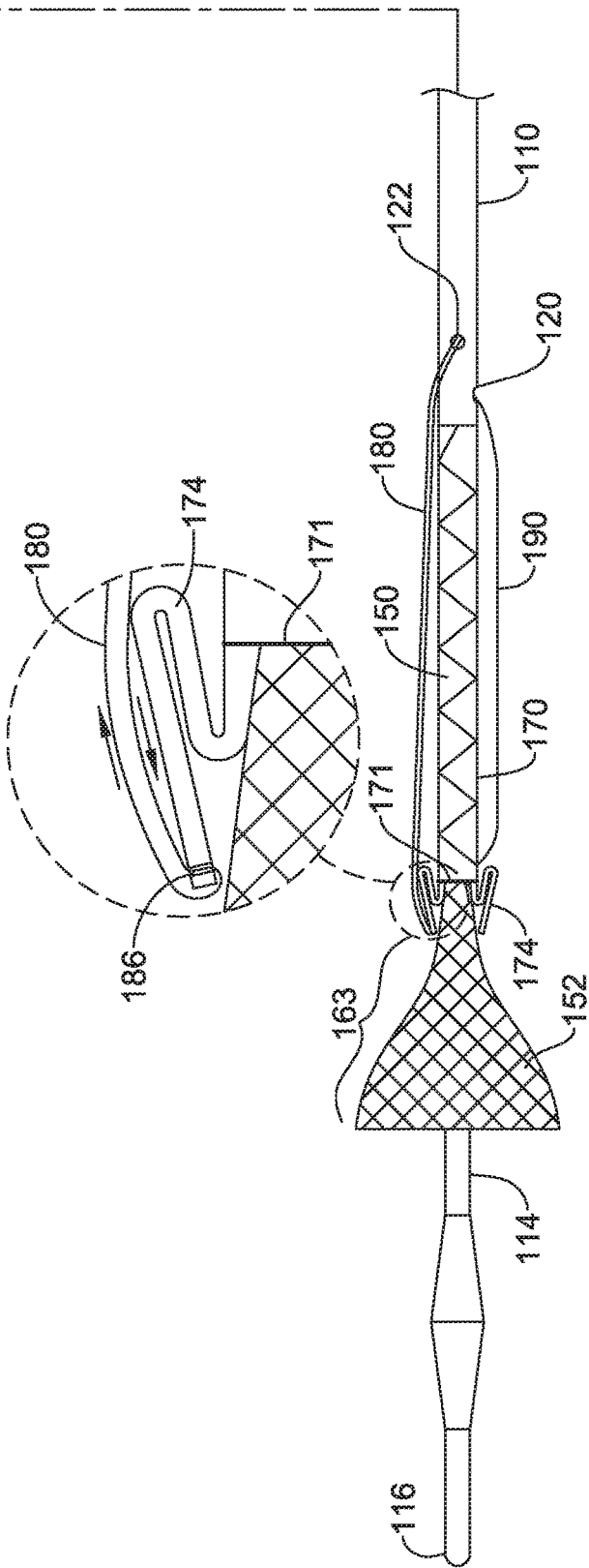
FIG. 15

STENT WITH SELECTIVELY COVERED REGION

CROSS-REFERENCE TO RELATED APPLICATIONS

This application claims the benefit of priority under 35 U.S.C. § 119 of U.S. Provisional Application No. 62/661,431, filed Apr. 23, 2018, the entire disclosure of which is hereby incorporated by reference.

TECHNICAL FIELD

The present disclosure pertains to stent with a selectively covered region. More particularly, the present disclosure pertains a stent including a removable skirt for exposing a distal end region of an expandable scaffold of the stent for hyperplastic tissue ingrowth.

BACKGROUND

Wounds may develop within the gastrointestinal system for a variety of reasons. For example, bariatric surgical procedures create staple lines that may be prone to leakage. In some cases, the presence of materials such as nutritional contents can interfere with healing of the staple lines. In some instances, the presence of nutritional contents can irritate healing tissue and can lead to infection. It may be helpful to protect the healing staple line from materials such as nutritional contents. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for stents and stent delivery devices.

A first example includes a stent including a radially expandable tubular framework having a proximal end, a distal end, and a lumen extending therethrough. The stent also includes a covering surrounding the tubular framework. The covering is affixed to the tubular framework at a first affixment location. The covering includes a proximal region extending proximal of the first affixment location and surrounding a medial region of the tubular framework. The covering also includes a skirt extending distal of the first affixment location and surrounding a distal end region of the tubular framework. The skirt is selectively removable from the distal end region of the tubular framework to expose the distal end region of the tubular framework.

Alternatively or additionally to any of the examples above, in another example, the skirt surrounds but is not directly affixed to the tubular framework distal of the first affixment location.

Alternatively or additionally to any of the examples above, in another example, the skirt is convertible from a first configuration in which the skirt surrounds the distal end region of the tubular framework and a second configuration in which the skirt is folded upon itself proximate the first affixment location.

Alternatively or additionally to any of the examples above, in another example, the skirt is convertible from a first configuration in which the skirt surrounds the distal end region of the tubular framework and a second configuration in which the skirt surrounds the proximal region of the covering proximal of the first affixment location.

Alternatively or additionally to any of the examples above, in another example, the covering includes a preferential tear line configured to selectively separate the skirt from the proximal region of the covering, the preferential tear line extending circumferentially around the covering distal of the first affixment location.

Alternatively or additionally to any of the examples above, in another example, a drawstring is attached to the skirt, wherein the drawstring extends along the tubular framework to the proximal end of the tubular framework, wherein manipulation of the drawstring removes the skirt from the distal end region of the tubular framework.

Alternatively or additionally to any of the examples above, in another example, the drawstring extends along the tubular framework between an inner surface of the proximal region of the covering and an outer surface of the tubular framework.

Alternatively or additionally to any of the examples above, in another example, the drawstring passes radially inward of the first affixment location as the drawstring passes distally from the proximal region of the covering to the skirt.

Alternatively or additionally to any of the examples above, in another example, a proximal end of the proximal region of the covering is affixed to the tubular framework at a second affixment location, wherein the second affixment location is spaced proximally away from the first affixment location.

Alternatively or additionally to any of the examples above, in another example, the skirt extends distal of the distal end of the tubular framework a distance of 20 millimeters or more.

Another example includes a stent including a radially expandable tubular framework having a proximal end, a distal end, and a lumen extending therethrough. The tubular framework includes a proximal end region extending to the proximal end of the tubular framework, a distal end region extending to the distal end of the tubular framework, and a cylindrical medial region extending between the proximal end region and the distal end region. The stent also includes a covering surrounding the tubular framework. The covering is affixed to the tubular framework at a first affixment location and at a second affixment location. The first affixment location is positioned proximate a junction between the distal end region and the medial region of the tubular framework and the second affixment location is positioned proximate a junction between the proximal end region and the medial region of the tubular framework. The covering includes a proximal region located proximal of the first affixment location and surrounding the medial region of the tubular framework. The covering includes a skirt located distal of the first affixment location and surrounding the distal end region of the tubular framework. The skirt is selectively removable from the distal end region of the tubular framework to expose the distal end region of the tubular framework.

Alternatively or additionally to any of the examples above, in another example, a proximal end of the covering is located at the second affixment location such that the proximal end region of the tubular framework is devoid of the covering and is uncovered to permit hyperplastic tissue ingrowth through the proximal end region of the tubular framework.

Alternatively or additionally to any of the examples above, in another example, a drawstring is attached to the skirt, wherein the drawstring extends along the tubular framework to the proximal end of the tubular framework, wherein manipulation of the drawstring removes the skirt from the distal end region of the tubular framework.

Alternatively or additionally to any of the examples above, in another example, the drawstring passes radially inward of the first and second affixment locations as the drawstring passes distally from the proximal end of the tubular framework to the skirt.

Alternatively or additionally to any of the examples above, in another example, the drawstring extends along the medial region of the tubular framework between an inner surface of the proximal region of the covering and an outer surface of the tubular framework.

Yet another example is a stent delivery system including an elongate shaft having a handle at a proximal end thereof, and a radially expandable stent disposed on a distal region of the elongate shaft. The stent includes a radially expandable tubular framework having a proximal end, a distal end, and a lumen extending therethrough. The stent also includes a covering surrounding the tubular framework. The covering is affixed to the tubular framework at a first affixment location. The covering includes a proximal region extending proximal of the first affixment location and surrounding a medial region of the tubular framework. The covering also includes a skirt extending distal of the first affixment location and surrounding a distal end region of the tubular framework. The skirt is selectively removable from the distal end region of the tubular framework to expose the distal end region of the tubular framework. A drawstring extends from the skirt to the handle. Manipulation of the drawstring removes the skirt from the distal end region of the tubular framework.

Alternatively or additionally to any of the examples above, in another example, a thread surrounds the stent to constrain the stent in a radially contracted configuration on the distal region of the elongate shaft.

Alternatively or additionally to any of the examples above, in another example, the drawstring loops through a grommet on the skirt.

Alternatively or additionally to any of the examples above, in another example, the drawstring passes through an opening into a lumen of the elongate shaft proximal of the stent and extends through the lumen of the elongate shaft to the handle.

Alternatively or additionally to any of the examples above, in another example, the skirt surrounds but is not directly affixed to the tubular framework distal of the first affixment location.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which:

FIG. 6A is a longitudinal cross-sectional view of the distal end region of the stent in FIG. 6;

FIG. 6B is an alternative longitudinal cross-sectional view of the distal end region of the stent in FIG. 6;

FIGS. 14-15 illustrate alternative steps of deploying a stent of the stent delivery system of FIG. 9.

Figure 1:
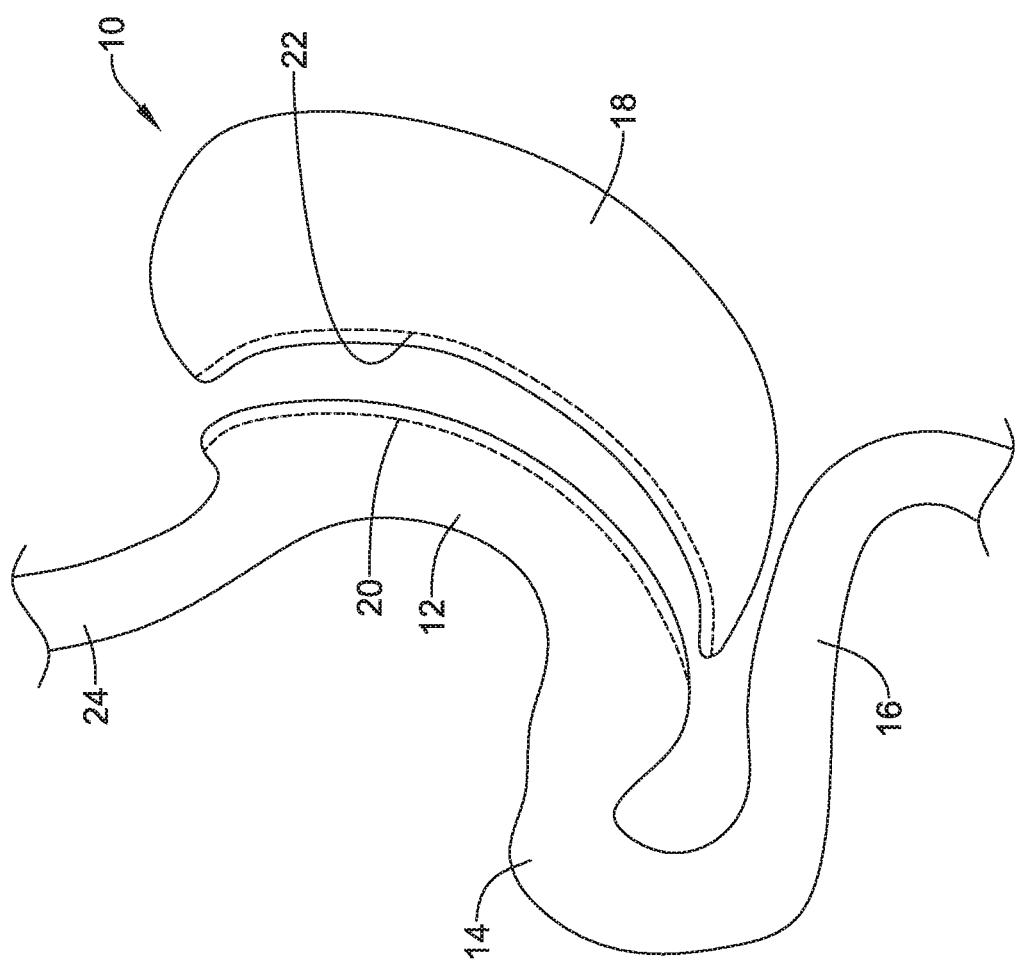
FIG. 1 is a schematic illustration of a gastric sleeve procedure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

There are a number of conditions, diseases and surgical interventions that may result in wounds such as a leak or an abscess within the gastrointestinal tract. In many cases, a surgical intervention may create a staple line or suture line within a portion of the gastrointestinal tract. An illustrative but non-limiting example of such a surgical intervention is bariatric surgery. In bariatric surgery, which may be performed as an open surgery or more commonly as a laproscopic surgery, an obese patient's stomach is made substantially smaller. As a result, the patient may be able to lose weight, particularly if they follow corresponding dietary restrictions. There are several common bariatric techniques including sleeve gastrectomy and Roux-en-Y.

FIG. 1 illustrates the results of a sleeve gastrectomy, in which a large portion of a patient's stomach 10 is cut away. As a result, a relatively small attached portion 12 of the patient's stomach 10 remains fluidly coupled through the pylorus 14 with the small intestine 16. As can be seen in FIG. 1, a relatively large resected portion 18 of the patient's stomach 10 is resected, or cut away from the attached portion 12 of the patient's stomach 10 that remains as part of the patient's effective gastrointestinal tract and extends from the esophagus 24 to the small intestine 16 It will be appreciated that as a result of the resection, a large staple line 20 is formed along one side of the small portion 12 of the patient's stomach 10. In some instances, a corresponding long staple line 22 may be formed along one side of the resected portion 18 of the patient's stomach 10.

Figure 2:
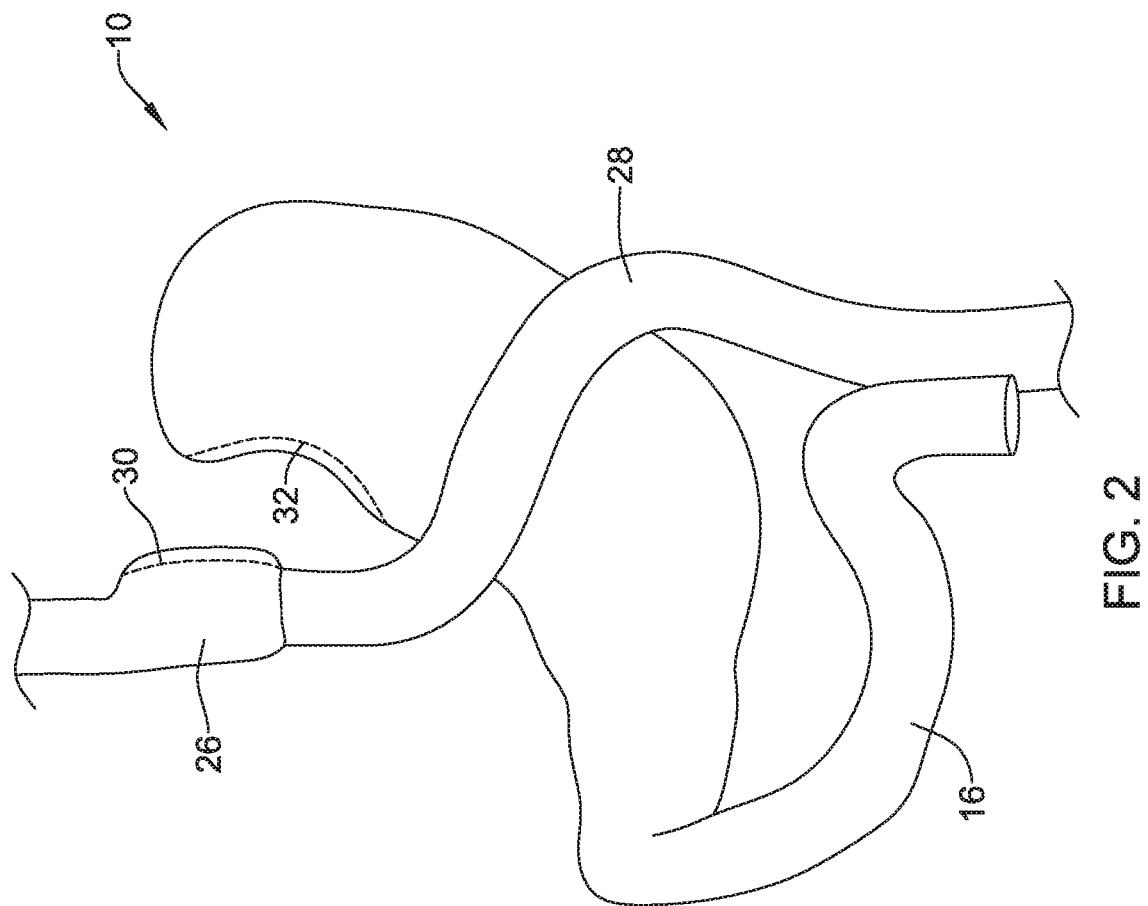
FIG. 2 is a schematic illustration of a Roux-en-Y procedure.

FIG. 2 illustrates the Roux-en-Y gastric bypass procedure in which an even larger portion of the patient's stomach 10 is resected and a portion of the small intestine 16 is also bypassed. In this procedure, a pouch 26 is formed from the very uppermost portion of the stomach 10 and is secured to the Roux limb 28, which is a portion of the small intestine 16 that is secured to the pouch 26. It will be appreciated that as a result of the resection, a staple line 30 is formed along one side of the pouch 26. A corresponding staple line 32 is formed along one side of the stomach 10.

It will be appreciated that leaks may occur along these staple lines, including the staple line 20 and the staple line 30. As a result, in some cases a pus-filled abscess may form adjacent the staple line 20 and/or the staple line 30. In some cases, it can be beneficial to place a stent, which in some cases may be a covered stent, proximate the wound in order to help seal off the leak, protect the wound from harsh stomach acids and keep nutritional contents such as food and beverages away from the wound. While leaks may occur along the staple line 22 and/or the staple line 32, it will be appreciated that this disclosure is directed to treating wounds that may be reached from inside the remaining gastrointestinal tract.

Figure 3:
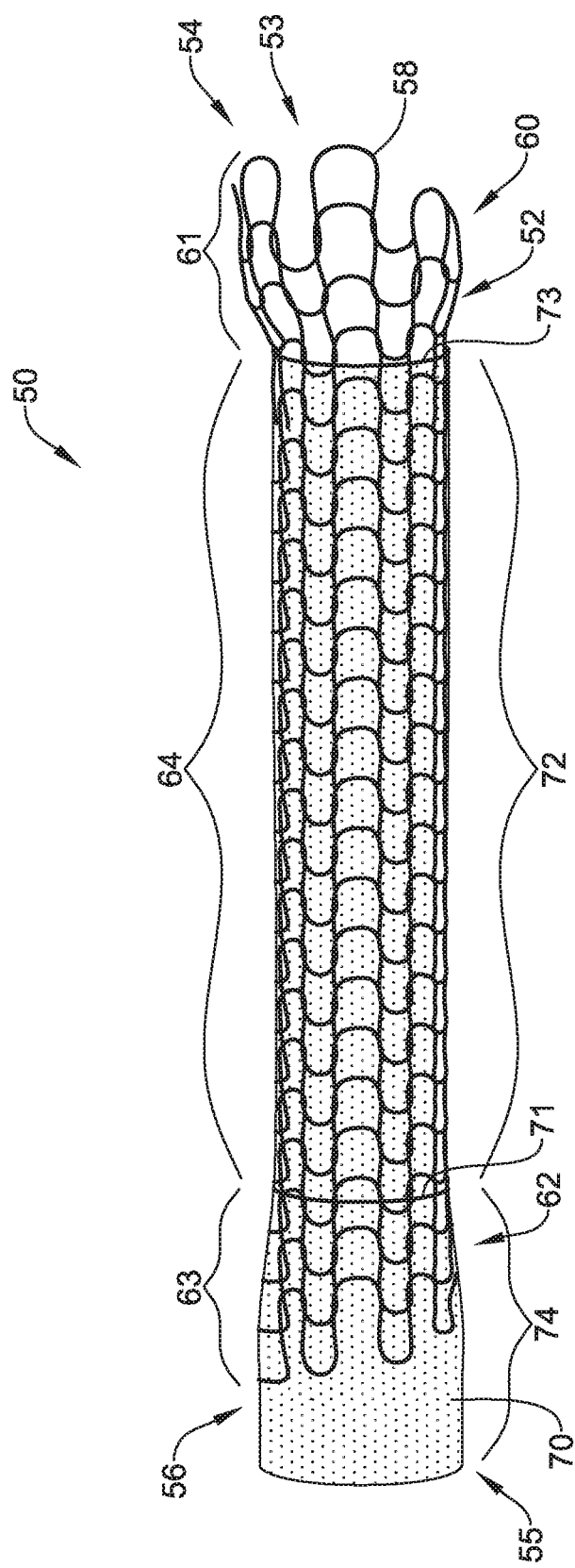
FIG. 3 is a side view of an exemplary stent having a skirt covering a distal end region of the tubular scaffold of the stent.

FIG. 3 shows an example stent 50 having a first end 53 and a second end 55 opposite the first end 53. The stent 50 may include a tubular scaffold 52 having a first end 54, which may be considered a proximal end in some instances, a second end 56, which many be considered a distal end in some instances, and a lumen extending therethrough. The first end 54 may be located proximate the first end 53 of the stent 50 and the second end 56 may be located proximate the second end 55 of the stent 50. The tubular scaffold 52 may be configured to provide the support structure for the stent 50. The tubular scaffold 52 may be formed of one or more stent filaments 58, or a plurality of stent filaments 58. The filament(s) 58 may extend longitudinally along the stent 50.

In some instances, the stent 50 may be a self-expanding stent in which the one or more filaments 58 are interwoven to form the tubular scaffold 52, having openings defined between adjacent filaments 58. For example, stent filaments 58 may be wires braided, knitted or otherwise interwoven to form the tubular scaffold 52. Openings or interstices through the wall of the tubular scaffold 52 may be defined between adjacent stent filaments 58. Alternatively, the tubular scaffold 52 of the stent 50 may be a monolithic structure formed from a cylindrical tubular member, such as a single, cylindrical tubular laser-cut Nitinol tubular member, in which the remaining portions of the tubular member form the stent struts with openings defined therebetween.

Additionally, FIG. 3 shows the example stent 50 including one or more enlarged portions (e.g., flares) of the expandable scaffold 52 proximate the first end 54 and/or the second end 56. For instance, the stent 50 may include a first flared region 60 at the first, proximal end region 61 of the expandable scaffold 52 extending to the first end 54 of the expandable scaffold 52 and/or a second flared region 62 at the second, distal end region 63 of the expandable scaffold 52 extending to the second end 56 of the expandable scaffold 52. In some instances, the enlarged or flared regions 60/62 may be defined as an increase in the outer diameter, the inner diameter or both the inner and outer diameter of the expandable scaffold 52 relative to a medial region 64 of the expandable scaffold 52 positioned between the first and second flared regions 60/62. In some instances, the medial region 64 may be a cylindrical region of the expandable scaffold 52 extending from the first flared region 60 to the second flared region 62 having an outer diameter less than an outer diameter of the first and second flared regions 60/62. In other instances, the medial region 64 may be a cylindrical region of the expandable scaffold 52 extending from the first flared region 64 to the second end 56 of the expandable scaffold 52 having an outer diameter less than an outer diameter of the first flared region 60. The flared regions 60/62 may be beneficial to anchor the stent 50 within the esophagus and/or the opening to the stomach, for example.

The tubular scaffold 52, such as the filaments 58, disclosed herein may be constructed from a variety of materials. For example, the tubular scaffold 52, or components thereof, may be constructed from a metal (e.g., Nitinol). In other instances, the tubular scaffold 52, or components thereof, may be constructed from a polymeric material (e.g., PET). In yet other instances, the tubular scaffold 52, or components thereof, may be constructed from a combination of metallic and polymeric materials. Additionally, the tubular scaffold 52, or components thereof, may include a bioabsorbable and/or biodegradable material.

Additionally, the stent 52 may include a covering 70 disposed on the tubular scaffold 52, such as positioned on and/or adjacent to the outer surface of the tubular scaffold 52 to thereby surround the tubular scaffold 52. The covering 70 may be positioned on a portion of the filaments 58 forming the tubular scaffold 52 and extend across openings or cells between adjacent filaments 58. In some instances, the covering 70 may be an elastomeric or non-elastomeric material. For example, the covering 70 may be a polymeric material, such as silicone, polyurethane, or the like. The covering 70 may isolate the lumen of the tubular scaffold 52 from the body lumen of the patient, thereby forming a barrier, such as a sealed interface, between the lumen of the tubular scaffold 52 and the portion of the body lumen positioned radially outward of the covering 70.

As described above, the stent 50 may have a first end 53 and a second end 55. When positioned in a body lumen (e.g., esophagus, stomach, stomach pouch, intestine, etc.) the first end 53 may be defined as the proximal end of the stent 50 and oriented as the end of the stent 50 closest to a patient's mouth and the second end 55 may be defined as the distal end of the stent 50 and oriented as the end of stent 50 closest to a patient's stomach.

As shown in FIG. 3, the covering 70 may be fixedly attached to the expandable scaffold 52 at one or more affixment locations. For instance, the covering 70 may be affixed to the expandable scaffold 52 at a first affixment location 71 and/or at a second affixment location 73. The first and second affixment locations 71/73 may be spaced apart from one another with the second affixment location 73 closer to the first, proximal end 53 of the stent 50 than the first affixment location 71, and the covering 70 extending between the first and second affixment locations 71/73 and circumferentially surrounding the expandable scaffold 52 between the first and second affixment locations 71/73. In some instances, the covering 70 may not be directly affixed to the tubular scaffold 52 between the first and second affixment locations 71/73. In some instances, the covering 70 may be affixed to the tubular scaffold 52 continuously around the entire circumference of the tubular scaffold 52 at the first and second affixment locations 71/73, or the covering 70 may be affixed at discrete circumferentially spaced locations around the circumference of the tubular scaffold 52 at the first and second affixment locations 71/73. In some embodiments, the covering 70 may be affixed to the expandable scaffold 52 with an adhesive at the first and/or second affixment locations 71/73. The first and second affixment locations 71/73 may be located intermediate the first and second ends 54/56 of the tubular scaffold 52, such that the tubular scaffold 52 extends proximal of the affixment locations 71/73 toward the first, proximal end 53 of the stent 50, and the tubular scaffold 52 extends distal of the affixment locations 71/73. For example, the first affixment location 71 may be located between the distal end region 63 and the medial region 64 of the tubular scaffold 52, and the second affixment location 73 may be located between the medial region 64 and the proximal end region 61 of the tubular scaffold 52. A portion of the covering 70, such as the proximal region 72 of the covering 70, may extend proximal of the first affixment location 71 toward the first end 53 of the stent 10 and circumferentially surround the medial region 64 of the expandable scaffold 52. The proximal end of the covering 70 may be affixed to the expandable scaffold 52 at the second affixment location 73. In some instances the second affixment location 73, and thus the proximal end of the covering 70, may be located proximate the junction between the medial region 64 and the proximal end region 61, and thus the flared end region 60, of the expandable scaffold 52, leaving the proximal end region 61, and thus the proximal flared end region 60 uncovered. Thus, the proximal end region 61 may be devoid of any covering and thereby permit tissue ingrowth through interstices or openings of the expandable scaffold 52 between adjacent filaments 58. In other words, in some instances the covering 70 may extend less than the entire length of the stent 50, if desired, leaving a portion of cells or interstices defined between filaments 58 of tubular scaffold 52 unfilled or open to promote hyperplastic tissue ingrowth. However, in other instances the covering 70 may extend to the proximal end of the stent 50 and surround the proximal flared region 60 if desired.

As further shown in FIG. 3, the covering 70 may also include a distal end portion extending from the first affixment location 71 toward the second end 55 of the stent 50. In some instances, the first affixment location 71 may be located proximate the junction between the medial region 64 and the distal end region 63, and thus the flared distal end region 62, of the expandable scaffold 52. The portion of the covering 70 extending distal of the first affixment location 71 may be considered a skirt 74. The skirt 74 may circumferentially surround the tubular scaffold 52 distal of the first affixment location 71. In some instances, the skirt 74 is not directly affixed to the tubular scaffold 52 that it circumferentially surrounds (e.g., the distal end region 63 of the tubular scaffold 52 extending to the distal end 56 of the tubular scaffold 52) such that the skirt 74 may be selectively removed from the underlying portion of the tubular scaffold 52 to selectively uncover the distal end region 63 of the tubular scaffold 52, as will be further described herein. In some instances, the skirt 74 may extend from the first affixment location 71 to the second, distal end 56 of the tubular scaffold 52, or may extend from the first affixment location 71 distally beyond the second, distal end 56 of the tubular scaffold 52. In some instances, the skirt 74 may extend distally beyond the distal end 56 of the tubular scaffold 52 a distance of about 10 mm or more, about 20 mm or more, about 30 mm or more, or about 40 mm or more, for example.

In some instances, the covering 70 may be a monolithic or unitary structure including both the proximal region 72 and the skirt 74. For example, in some embodiments, the skirt 74 and the proximal region 72 may be formed of a singular polymeric member. However, in other instances, the skirt 74 may be formed from a discrete polymeric member separate from the polymeric member forming the proximal region 72.

Figure 4:
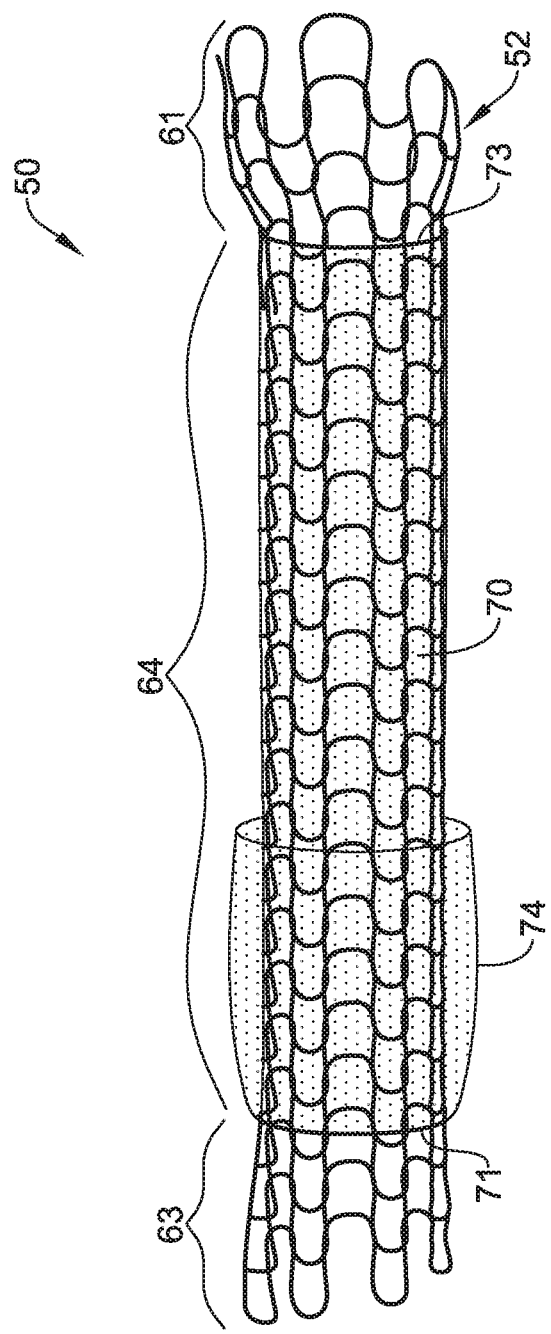
FIG. 4 is a side view of the exemplary stent of FIG. 3 with the skirt removed from the distal end region of the tubular scaffold of the stent.

As shown in FIG. 4, the skirt 74 may be selectively removed from the distal end region 63 of the tubular scaffold 52 to uncover or expose the distal end region 63 of the tubular scaffold 52 in instances in which it is desired to promote hyperplastic tissue ingrowth within the distal end region 63 upon implantation of the stent 50 in a body lumen of a patient. Alternatively, if it is desired to maintain the distal end region 53 covered by the skirt 74, the skirt 74 may be selectively retained or placed around the distal end region 63. Thus, the stent 50 may be selectively modified by surgical personnel during a medical procedure based on the desire to promote hyperplastic tissue sealing around the distal end region 63 of the tubular scaffold 52. In some instances, as shown in FIG. 4, the skirt 74 may be rolled back or drawn proximally over the medial region 64 of the tubular scaffold 52 proximal of the first affixment location 71, permitting the skirt 74 to circumferentially surround the covering 70 extending proximal of the first affixment location 71 along the medial region 64 of the tubular scaffold 52.

Figure 5:
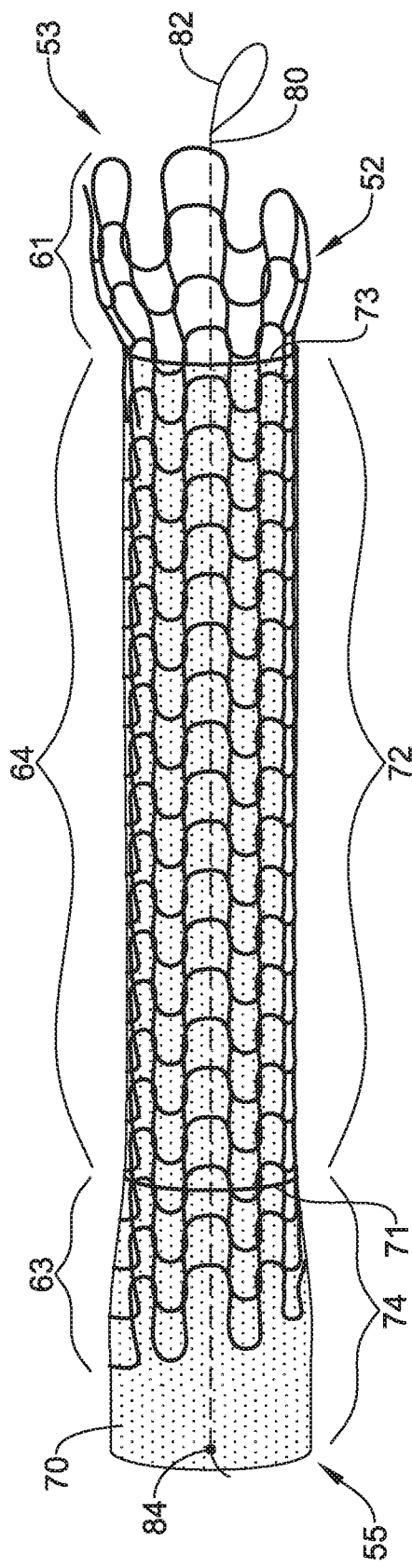
FIG. 5 is a side view of the exemplary stent having a skirt covering a distal end region of the tubular scaffold of the stent.

An alternative configuration of the stent 50 is shown in FIG. 5, wherein one or more drawstrings 80 are attached to the skirt 74 proximate the distal end 55 of the stent 50 and extend along the stent 50 to or beyond the proximal end 53 of the stent 50. For instance, a distal end of the drawstring 80 may be attached to the skirt 74 at an attachment location 84 and a proximal end of the drawstring 80 may include a pull 82, such as a loop, for grasping by medical personnel. The drawstring(s) 80 may be manipulated by surgical personnel (e.g., pulled proximally relative to the tubular scaffold 52) to selectively expose the distal end region 63 of the tubular scaffold 52 during a surgical procedure. For example, the drawstring(s) 80 may be pulled proximally to fold up the skirt 74.

Figure 6:
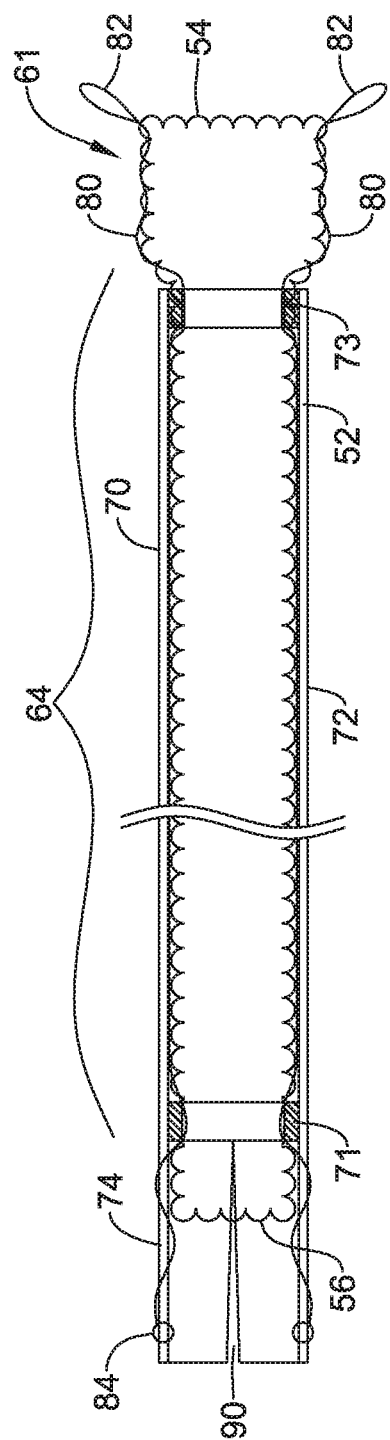
FIG. 6 is a longitudinal cross-sectional view of the stent of FIG. 5.

FIG. 6 is a cross-sectional view of the stent 50 of FIG. 5 showing one exemplary pathway for routing the drawstrings 80 along the stent 50. As shown in FIG. 6, in some instances, the drawstrings 80 may be woven in and out of the uncovered proximal end region 61 of the tubular scaffold 52 such that the drawstrings 80 pass radially outward of the tubular scaffold 52 and radially inward of the tubular scaffold 52 along the uncovered proximal region 61. In other instances, the drawstrings 80 may pass along an exterior of and thus radially outward of the uncovered proximal region 61, or the drawstrings 80 may pass along an interior of and thus radially inward of the uncovered proximal end region 61. The drawstrings 80 may pass radially inward of the second affixment location 73, and thus radially inward of the tubular scaffold 52, as the drawstrings 80 pass from the uncovered proximal region 61 to the covered medial region 64 of the tubular scaffold 52. Furthermore, the drawstrings 80 may pass radially outward through the tubular scaffold 52 distal of the second affixment location 73 such that the drawstrings 80 may extend radially inward of the medial region 72 of the covering 70 between the inner surface of the covering 70 and the outer surface of the expandable scaffold 52 throughout the medial region 64 of the expandable scaffold 52 between the first and second affixment locations 71/73. The drawstrings 80 may pass radially inward of the first affixment location 71, and thus radially inward of the tubular scaffold 52, as the drawstrings 80 passes the first affixment location 71 to the skirt 74. The drawstrings 80 may be passed outward and inward through the wall of the skirt 74 one or more, or a plurality of times as the drawstrings 80 are routed along the skirt 74 to the attachment location 84.

Further shown in FIG. 6, in some instances the skirt 74 of the covering 70 may include one or more slits 90 to facilitate removing the skirt 74 from the distal end region 63. In other instances, the skirt 74 may include perforation lines, preferential tear lines, weakened areas, or other structural characteristics permitting portions of the skirt 74 to be separated to facilitate removing the skirt 74 from the distal end region 63. It is understood that any of the embodiments described herein, may include slits, perforation lines, preferential tear lines, weakened areas, or other structural characteristics permitting portions of the skirt 74 to be separated to facilitate removing the skirt 74 from the distal end region 63.

As shown in FIG. 6A, the skirt 74 may be selectively removed from the distal end region 63 of the tubular scaffold 52 to uncover or expose the distal end region 63 of the tubular scaffold 52 in instances in which it is desired to promote hyperplastic tissue ingrowth within the distal end region 63 upon implantation of the stent 50 in a body lumen of a patient. For instance, as shown in FIG. 6A, the drawstrings 80 may be pulled proximally relative to the tubular scaffold 52 to fold the skirt 74 proximate the first affixment location 71. For example, the skirt 74 may be folded one or more times upon itself to expose the distal end region 63.

An alternative arrangement of the drawstrings 80 along the skirt 70 is shown in FIG. 6B, in which the drawstrings 80 extend along an interior surface of the skirt 70 distal of the first affixment location 71 to the attachment location 84. As shown in FIG. 6B, the skirt 74 may be selectively removed from the distal end region 63 of the tubular scaffold 52 to uncover or expose the distal end region 63 of the tubular scaffold 52 in instances in which it is desired to promote hyperplastic tissue ingrowth within the distal end region 63 upon implantation of the stent 50 in a body lumen of a patient. For instance, as shown in FIG. 6B, the drawstrings 80 may be pulled proximally relative to the tubular scaffold 52 to fold the skirt 74 proximate the first affixment location 71. For example, the skirt 74 may be folded one or more times upon itself to expose the distal end region 63.

Figure 7:
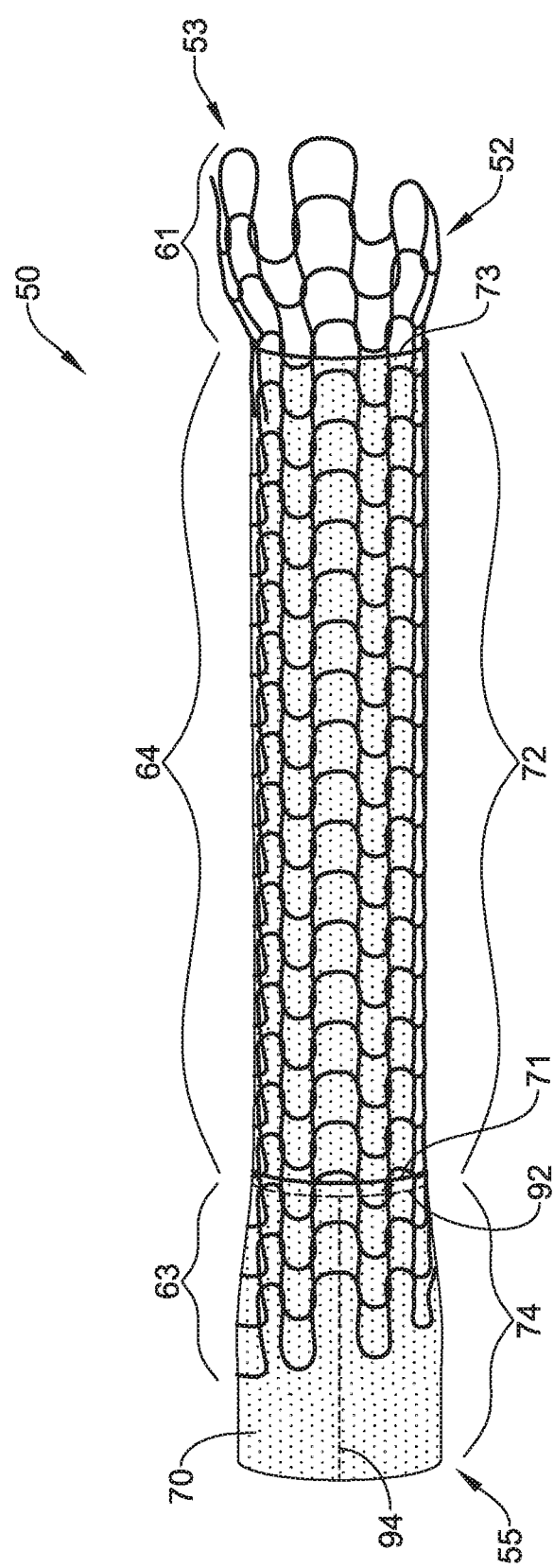
FIG. 7 is a side view of the exemplary stent having a skirt covering a distal end region of the tubular scaffold of the stent.
Figure 8:
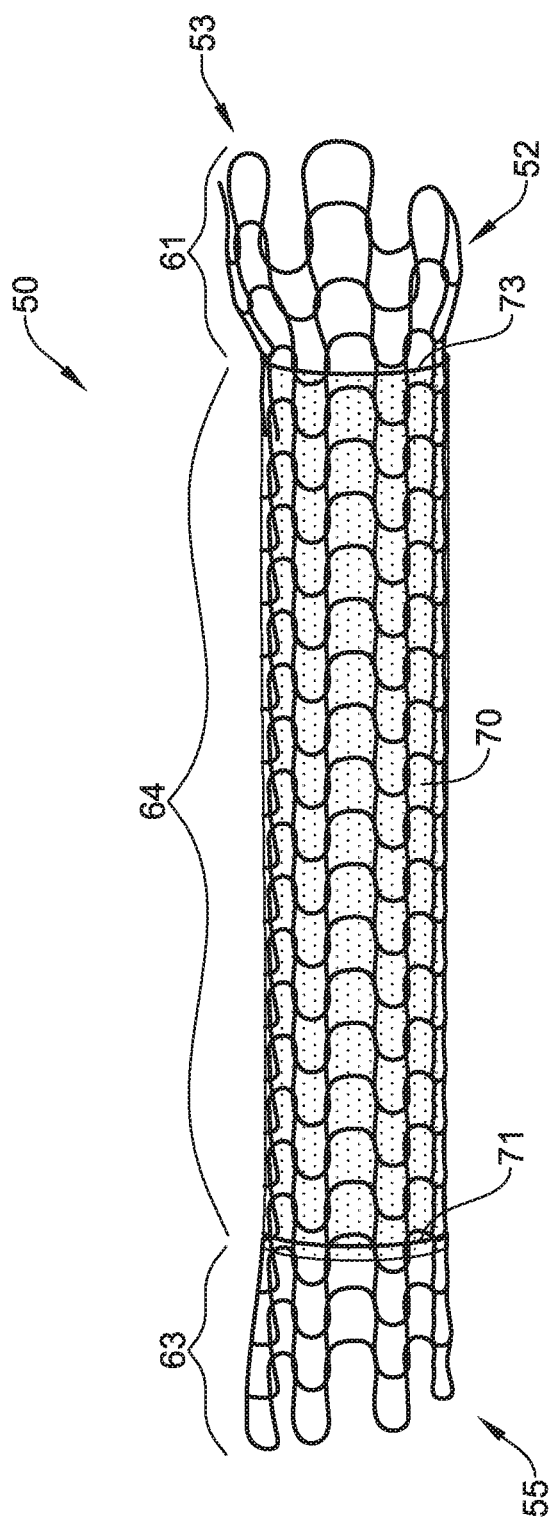
FIG. 8 is a side view of the exemplary stent of FIG. 7 with the skirt removed from the distal end region of the tubular scaffold of the stent.

An alternative configuration of the stent 50 is shown in FIG. 7, wherein the covering 70 includes one or more, or a plurality a preferential tears lines to facilitate selectively removing the skirt 74 from the remainder of the covering 70 (i.e., separating the skirt 74 from the proximal region 72 of the covering 70). The preferential tear line(s) may include a perforation line, weakened region, score line, or other structural characteristics to preferentially separate the skirt 74 from the remainder of the covering 70 along the preferential tear line(s). For instance, the covering 70 may include a preferential tear line 92 extending circumferentially around the covering 70 distal of the first affixation location 71. Additionally, in some embodiments, the skirt 74 may include one or more preferential tear lines 94 extending to the distal end of the skirt 74, such as longitudinally or helically to the distal end of the skirt 74. The preferential tear lines 92/94 may be used to separate the skirt 74 from the proximal region 72 of the covering 70 by surgical personnel to selectively expose the distal end region 63 of the tubular scaffold 52 during a surgical procedure. FIG. 8 shows the stent 50 with the skirt 74 removed to expose or uncover the distal end region 63 of the tubular scaffold 52.

Figure 9:
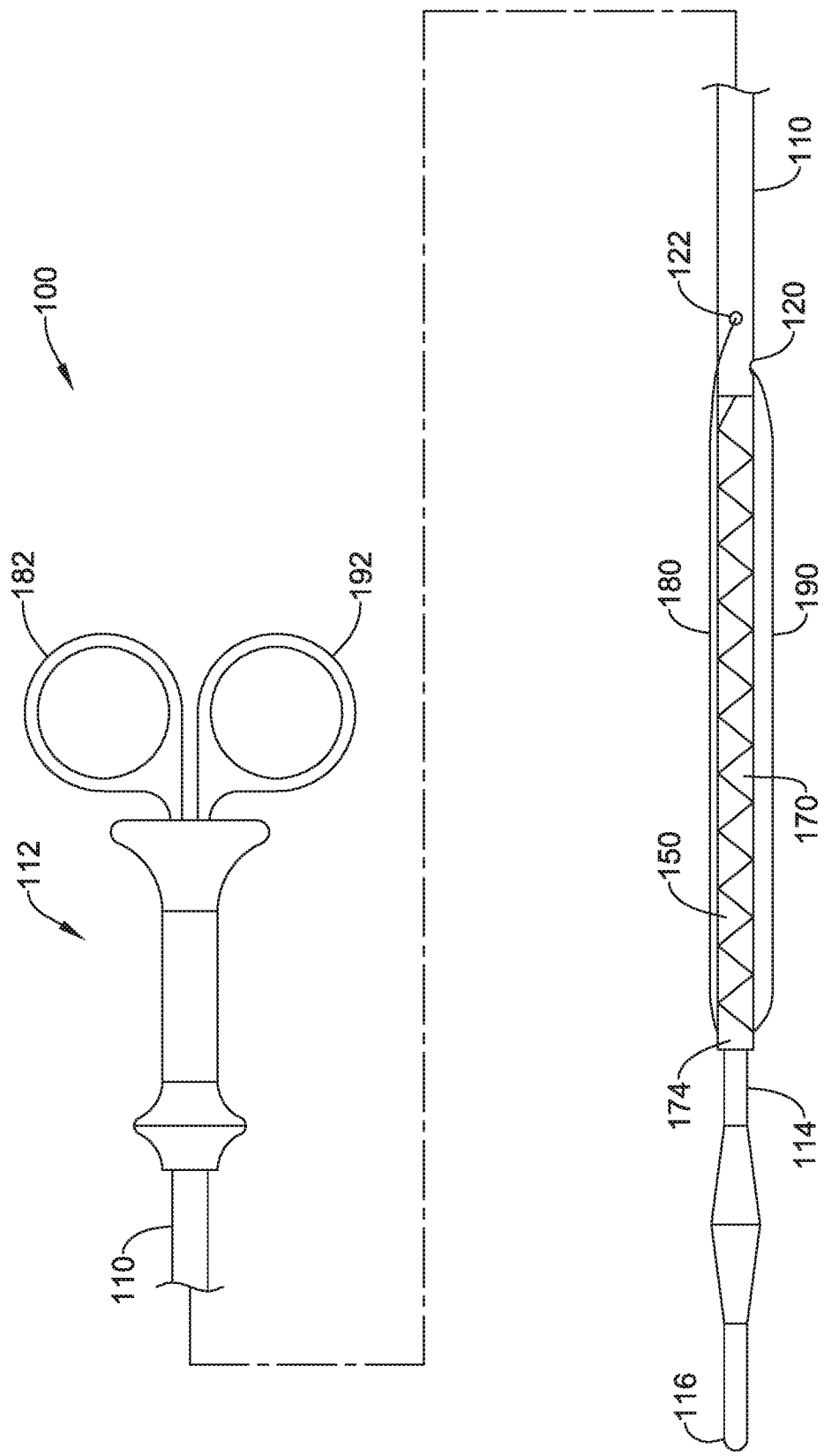
FIG. 9 is a side view of a stent delivery system.

An exemplary stent delivery system 100 is shown in FIG. 9. The stent delivery system 100 may include an elongate shaft 110, such as an elongate tubular member, extending distally from a handle 112 to a distal tip 116. For instance, a proximal end of the elongate shaft 110 may be affixed to the handle 112 and a distal end of the elongate shaft 110 may be located at the distal tip 116.

A radially expandable stent 150 may be disposed on and surround a distal end region 114 of the elongate shaft 110. The radially expandable stent 150 may be similar to the stent 50 described above in many respects. Accordingly, features of the stent 50 described above are equally applicable to the stent 150. For instance, the stent 150 may include an expandable tubular framework 152 and a covering 170 surrounding the tubular framework 152, as will be described further herein. The covering 170 may include a proximal region 172 covering a medial region of the tubular framework 152 and a skirt 174 covering a distal end region 163 of the tubular framework 152. A drawstring 180 may be attached to the skirt 174 at an attachment location proximate the distal end of the skirt 174. The drawstring 180 may extend along the elongate shaft 110 from the attachment location of the skirt 174 to the handle 112. The drawstring 180 may be attached to a pull member 182, or other actuator, at the handle 112 for longitudinal manipulation of the drawstring 180 relative to the tubular scaffold 152 of the stent 150 and the elongate shaft 110. In some instances, the elongate shaft 110 may include an opening 122 extending into an interior of the elongate shaft 110. The opening 122 may be located proximal of the stent 150. The drawstring 180 may pass through the opening 122 into a lumen of the elongate shaft 110, and pass within the lumen of the elongate shaft 110 to the pull member 182 at the handle 112. A distal region of the drawstring 180 may extend distal of the opening 122 exterior of the elongate shaft 110 to the attachment location of the skirt 174 proximate the distal end of the stent 150.

The stent delivery system 100 may also include a thread 190 surrounding the stent 150 to constrain the stent 150 in a radially contracted configuration on the distal end region 114 of the elongate shaft 110. For instance, the thread 190 may be crocheted or otherwise releasably secured around the stent 150 in a fashion that permits the crocheted portion of the thread 190 to unravel in a distal to proximal direction upon proximal manipulation of the thread 190. For instance, a proximal end of the thread 190 may be attached to a pull member 192, or other actuator, at the handle 112 for longitudinal manipulation of the thread 190 relative to the tubular scaffold 152 of the stent 150 and the elongate shaft 110. In some instances, the elongate shaft 110 may include an opening 120 extending into an interior of the elongate shaft 110. The opening 120 may be located proximal of the stent 150. The thread 190 may pass through the opening 120 into a lumen of the elongate shaft 110, and pass within the lumen of the elongate shaft 110 to the pull member 192 at the handle 112. A distal region of the thread 190 may be crocheted around the stent 150 in a fashion that permits the thread 190 to be controllably unraveled when the pull member 192 is actuated proximally relative to the handle 112.

The stent 150 may be delivered to a treatment location loaded on the elongate shaft 110 in the radially contracted configuration shown in FIG. 9. Once positioned at the treatment location, the medical personnel may actuate the thread 190 to initiate deployment of the stent 150 at the treatment location. For example, the medical personnel may pull the pull member 192 proximally relative to the handle 112 to begin unraveling the crocheted portion of the thread 190 from the distal end region of the stent 150 in a distal to proximal direction. The thread 190 may be removed from surrounding the stent 150 up to a location proximal of the distal end region 163 of the tubular scaffold 152 of the stent 150, permitting the distal end region of the stent 150 to at least partially radially expand. For example, the thread 190 may be removed from surrounding the stent 150 to a location proximal of the first affixment location 171 in which the covering 170 is affixed to the tubular scaffold 152. If it is desired to fully deploy the stent 150 with the distal end region 163 of the tubular scaffold 152 surrounded by, and thus covered by, the skirt 174, the thread 190 may be continued to be withdrawn proximally to completely unravel the crocheted portion surrounding the stent 150, allowing the stent 150 to radially expand along the entire length of the stent 150.

Figure 10:
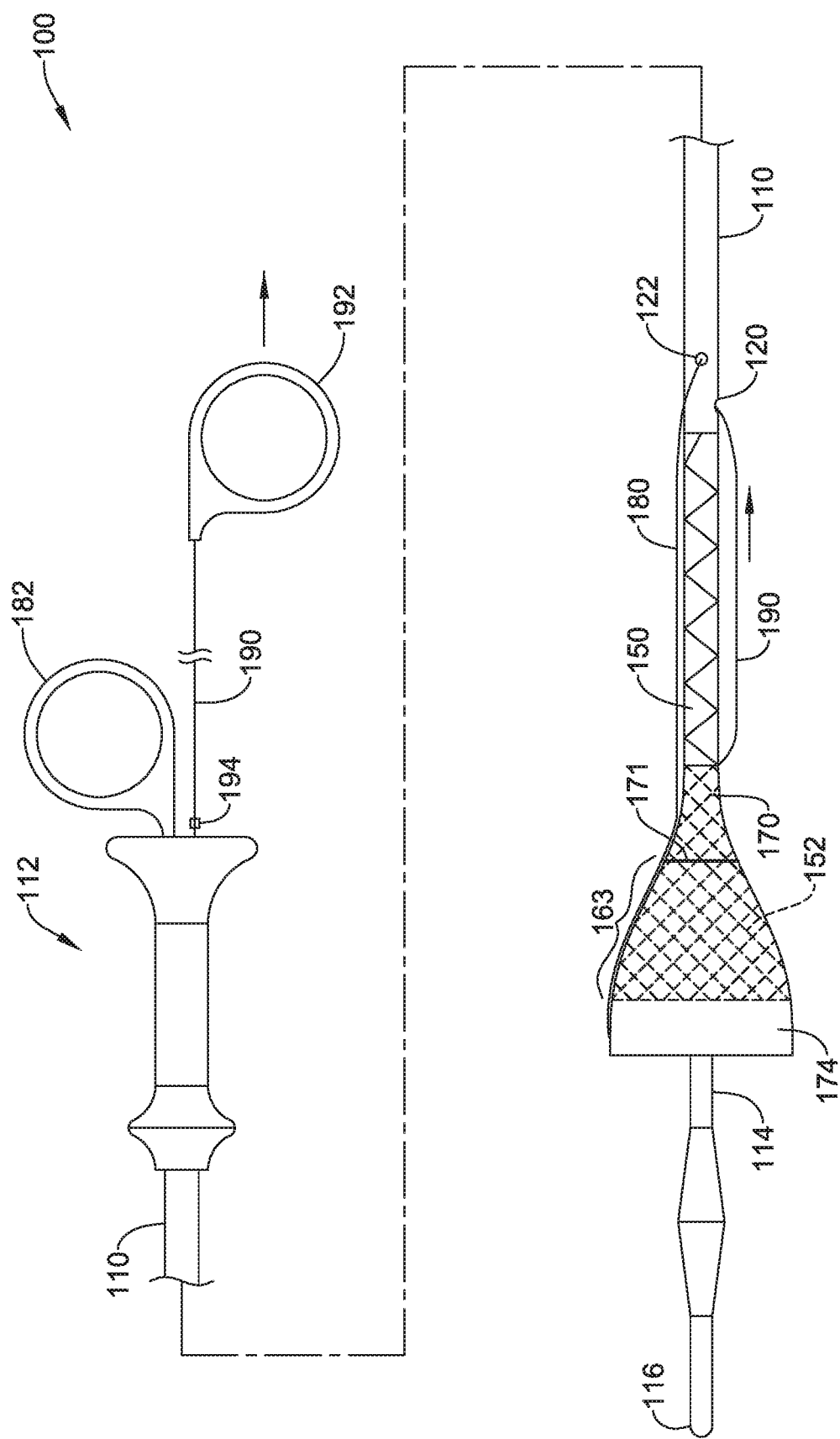
FIGS. 10-13 illustrate steps of deploying a stent with the stent delivery system of FIG. 9.

However, if it is desired to deploy the stent 150 with the skirt 174 removed from the distal end region 163 of the tubular scaffold 152, and thus uncovered to permit tissue ingrowth into and around the distal end region 163, unravelling of the crocheted portion of the thread 190 surrounding the stent 150 may be discontinued once the skirt 174 has been released from the thread 190. For example, the thread 190 may be removed from surrounding the stent 150 to a location proximal of the first affixment location 171 in which the covering 170 is affixed to the tubular scaffold 152, as shown in FIG. 10, permitting the distal end region 163 of the tubular framework 152 to at least partially radially expand. In some instances, the thread 190 may include a marker 194 or other visual indicia that can be used by the medical personnel to confirm the crocheted portion of the thread 190 has been sufficiently unraveled to expose the skirt 174.

Figure 11:
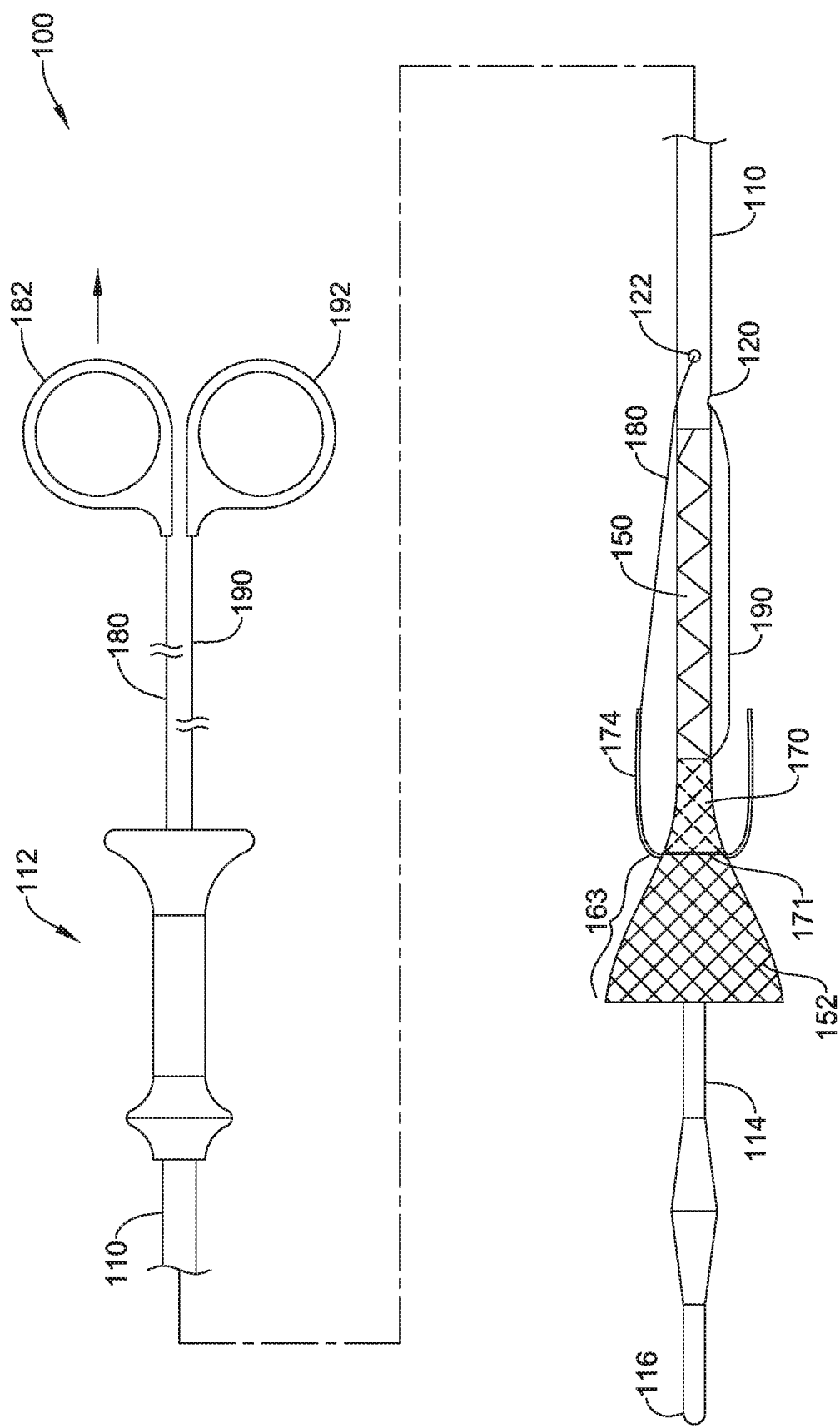

Once the skirt 174 has been uncovered from the crocheted portion of the thread 190, the drawstring 180 may be withdrawn proximally relative to the tubular scaffold 152 and the elongate shaft 110 to remove the skirt 174 from the distal end region 163 of the tubular scaffold 152. For example, the medical personnel may grasp the pull member 182 and actuate the pull member 182 proximally relative to the handle 112. As shown in FIG. 11, proximal retraction of the drawstring 180 causes the skirt 174 to be drawn proximal of the first affixment location 171 to expose the distal end region 163 of the tubular scaffold 152 of the stent 150.

Figure 12:
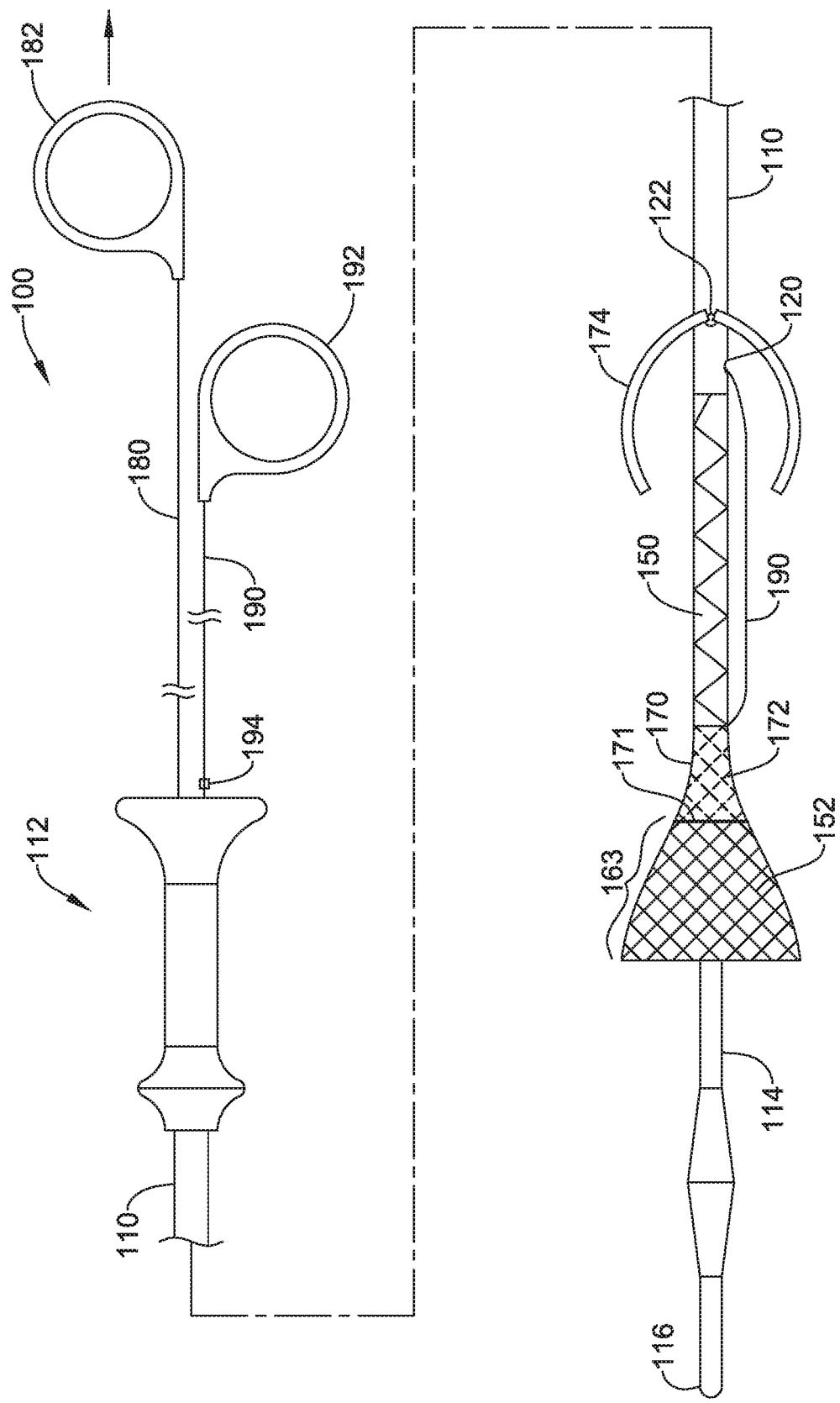

Further proximal retraction of the drawstring 180 may cause the skirt 174 to detach from the proximal region of the covering 170, as shown in FIG. 12. For example, similar to the configuration shown above at FIGS. 7 and 8, the skirt 174 may be removed from the remainder of the covering 170 along a preferential tear line (e.g., a circumferential tear line) of the covering 170 located distal of the first affixment location 171.

Figure 13:
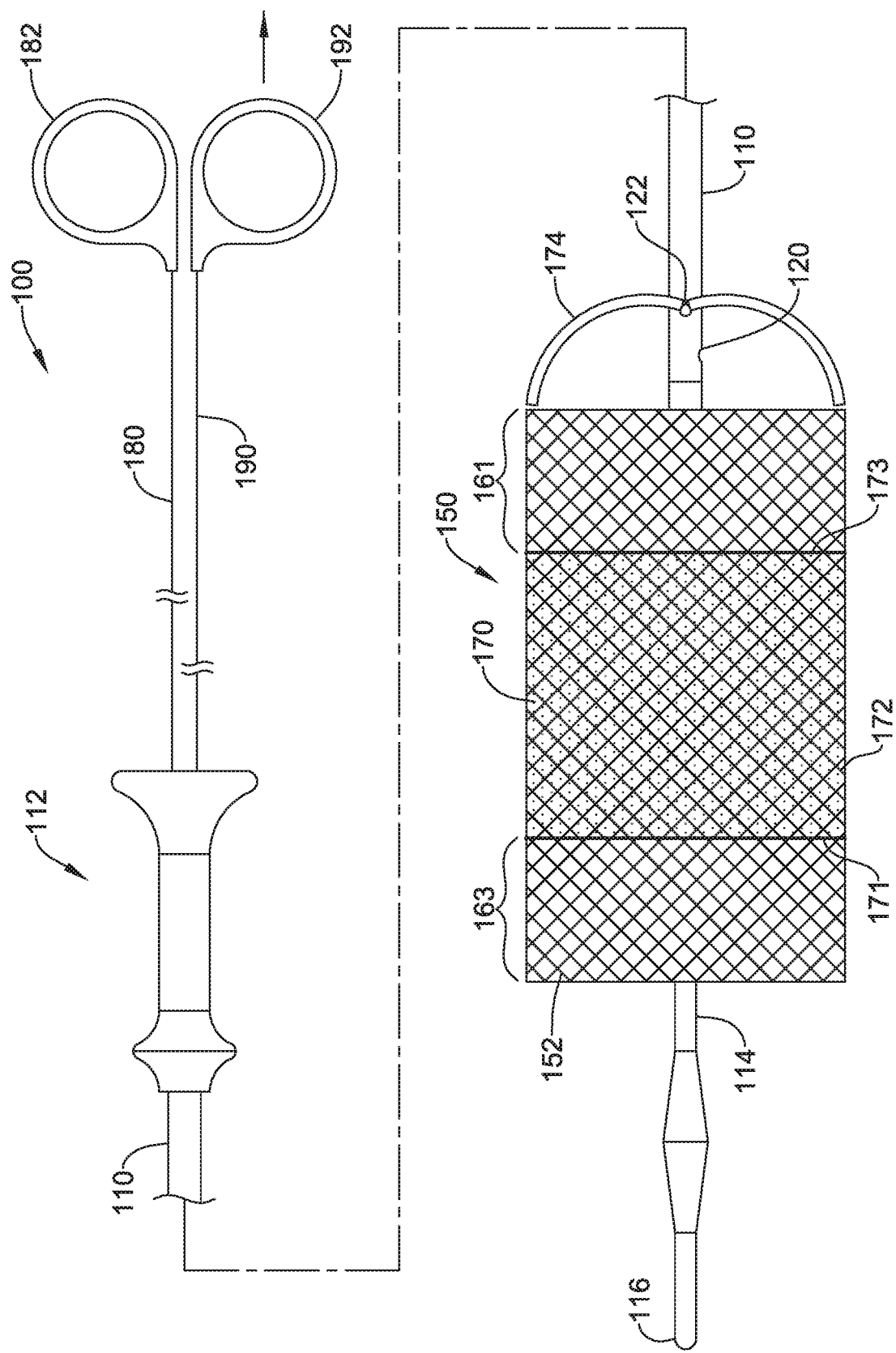

Thereafter, the thread 190 may be further withdrawn proximally to fully unravel the crocheted portion surrounding the proximal portion of the stent 150 to permit the entire stent 150 to radially expand at the treatment location. For example, as shown in FIG. 13, the medical personnel may pull the pull member 192 proximally relative to the handle 112 to continue unraveling the crocheted portion of the thread 190 from the proximal end region of the stent 150 in a distal to proximal direction until the crocheted portion is completely removed from the stent 150. Thus, the fully expanded stent 150 may include an uncovered distal end region 163 devoid of the skirt 174 or other covering which allows tissue ingrowth therein. Furthermore, in some instances, the stent 150 may include an uncovered proximal end region 161 of the tubular scaffold 152 devoid of the covering 170 or other covering which allows tissue ingrowth therein, while the medial region of the tubular scaffold 152 may be surrounded by the proximal region 172 of the covering 170 to prevent tissue ingrowth therein and provide a barrier between the interior of the stent 150 and surrounding anatomy at the treatment location. In some instances, the covering 170 may be affixed to the tubular scaffold 152 at a second affixment location 173 at the proximal end of the covering 170, spaced apart from the first affixment location 171. In some instances, the proximal region 172 of the covering 170 between the first and second affixment locations 171/173 may not be directly affixed to the tubular scaffold 152.

Once the stent 150 has been fully deployed at the treatment location, the elongate shaft 110 may be withdrawn from the body lumen along with the skirt 174 removed from the stent 150. For example, the skirt 174 may remain attached to the drawstring 180 as the elongate shaft 110 is withdrawn from the treatment location. Thus, the skirt 174 may be withdrawn from the body lumen of the patient at the conclusion of the medical procedure.

Figure 14:
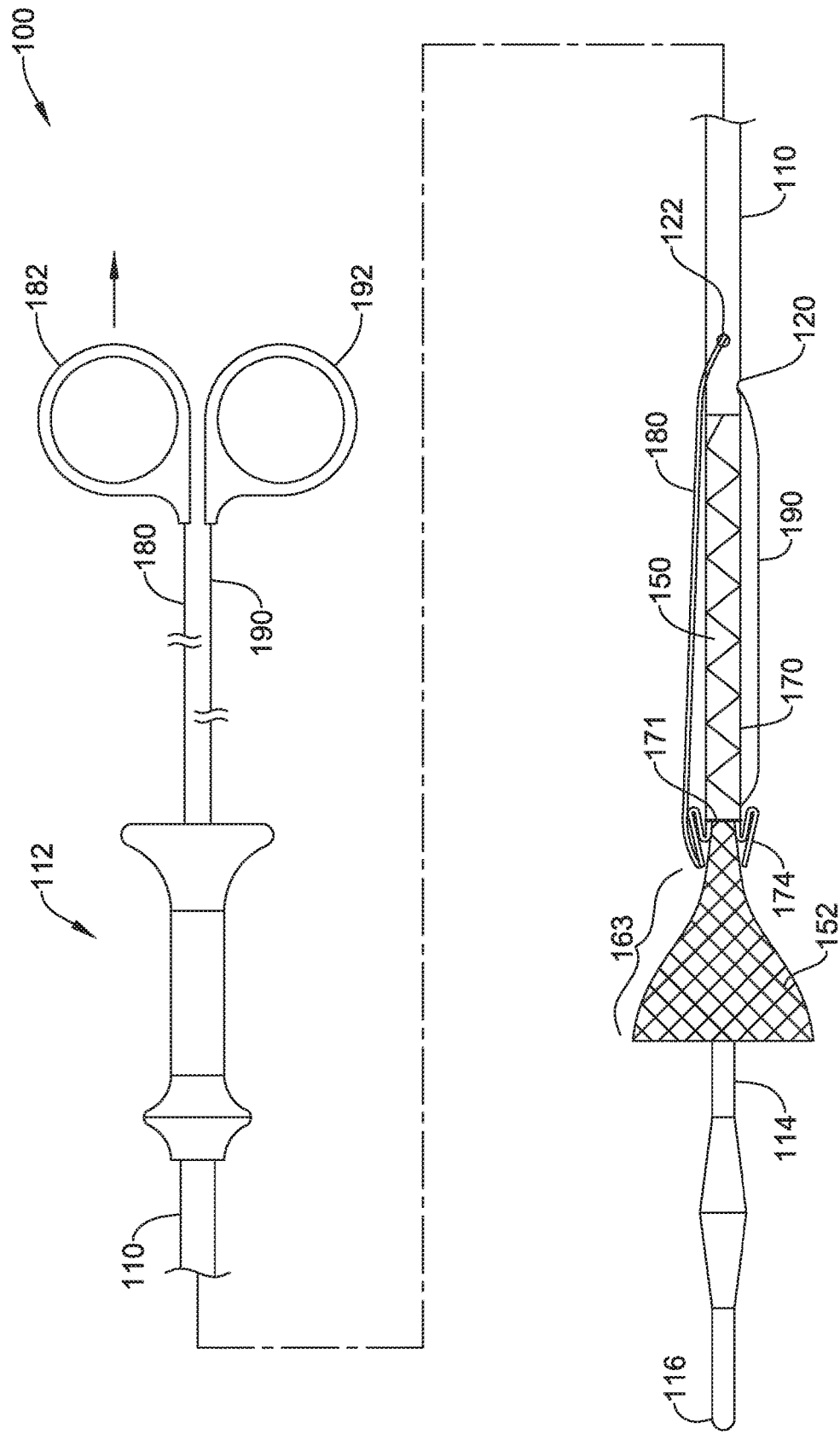

FIGS. 14 and 15 illustrate an alternative configuration for removing the skirt 174 from the distal end region 163 of the tubular scaffold 152 of the stent 150. As shown in FIG. 14, the skirt 174 may be retracted proximally by folding the skirt 174 upon itself proximate the first affixment location 171. For instance, the drawstring 180, which is attached to a distal end of the skirt 174, may be withdrawn proximally by proximal actuation of the pull member 182 relative to the handle 112 uncover the distal end region 163 of the tubular scaffold 152 of the stent 150.

Thereafter, the drawstring 180 may be detached from the skirt 174 and removed with the removal of the elongate shaft 110. For example, as shown in FIG. 15, the drawstring 180 may extend distal from the pull member 182 along the elongate shaft 110, may pass through an opening 186 of the skirt 174, and then may extend proximally from the opening 186 back to the pull member 182, forming a loop. In some instances, the opening may be a grommet attached to the skirt 174, having a hole therethrough for passing the drawstring 180. When it is desired to remove the drawstring 180 from the skirt 174, the loop of the drawstring 180 may be cut, such as proximate the handle 112, permitting one end of the drawstring 180 to be pulled through the opening 186 and back to the proximal end of the elongate shaft 110 and back to the handle 112, as shown by the arrows in FIG. 15.

Thereafter, as described above with regard to FIG. 13, the thread 190 may be further withdrawn proximally to fully unravel the crocheted portion surrounding the proximal portion of the stent 150 to permit the entire stent 150 to radially expand at the treatment location. For example, the medical personnel may pull the pull member 192 proximally relative to the handle 112 to continue unraveling the crocheted portion of the thread 190 from the proximal end region of the stent 150 in a distal to proximal direction until the crocheted portion is completely removed from the stent 150.

Once the stent 150 has been fully deployed at the treatment location, the elongate shaft 110 may be withdrawn from the body lumen leaving the skirt 174 folded upon itself proximate the first affixment location 171 and the distal end region 153 of the stent 150 exposed to permit tissue ingrowth therein.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent comprising:
a radially expandable tubular framework having a proximal end, a distal end, and a lumen extending therethrough; and
a covering surrounding the tubular framework, the covering being affixed to the tubular framework at a first affixment location;
the covering including a proximal region extending proximal of the first affixment location and surrounding a medial region of the tubular framework;
the covering including a skirt extending distal of the first affixment location and surrounding a distal end region of the tubular framework;
wherein the skirt is selectively removable from the distal end region of the tubular framework to expose the distal end region of the tubular framework; and
a drawstring attached to the skirt, wherein the drawstring extends along the tubular framework to the proximal end of the tubular framework, wherein manipulation of the drawstring removes the skirt from the distal end region of the tubular framework;
wherein the drawstring extends along the tubular framework between an inner surface of the proximal region of the covering and an outer surface of the tubular framework.

2. The stent of claim 1, wherein the skirt surrounds but is not directly affixed to the tubular framework distal of the first affixment location.

3. The stent of claim 1, wherein the skirt is convertible from a first configuration in which the skirt surrounds the distal end region of the tubular framework and a second configuration in which the skirt is folded upon itself proximate the first affixment location.

4. A stent comprising:
a radially expandable tubular framework having a proximal end, a distal end, and a lumen extending therethrough; and
a covering surrounding the tubular framework, the covering being affixed to the tubular framework at a first affixment location;
the covering including a proximal region extending proximal of the first affixment location and surrounding a medial region of the tubular framework;
the covering including a skirt extending distal of the first affixment location and surrounding a distal end region of the tubular framework;
wherein the skirt is selectively removable from the distal end region of the tubular framework to expose the distal end region of the tubular framework;
wherein the skirt is convertible from a first configuration in which the skirt surrounds the distal end region of the tubular framework and a second configuration in which the skirt surrounds the proximal region of the covering proximal of the first affixment location.

5. A stent comprising:
a radially expandable tubular framework having a proximal end, a distal end, and a lumen extending therethrough;
a covering surrounding the tubular framework, the covering being affixed to the tubular framework at a first affixment location;
the covering including a proximal region extending proximal of the first affixment location and surrounding a medial region of the tubular framework;
the covering including a skirt extending distal of the first affixment location and surrounding a distal end region of the tubular framework;
wherein the skirt is selectively removable from the distal end region of the tubular framework to expose the distal end region of the tubular framework; and
a preferential tear line configured to selectively separate the skirt from the proximal region of the covering, the preferential tear line extending circumferentially around the covering distal of the first affixment location.

6. The stent of claim 1, wherein the drawstring passes radially inward of the first affixment location as the drawstring passes distally from the proximal region of the covering to the skirt.

7. The stent of claim 1, wherein a proximal end of the proximal region of the covering is affixed to the tubular framework at a second affixment location, wherein the second affixment location is spaced proximally away from the first affixment location.

8. The stent of claim 1, wherein the skirt extends distal of the distal end of the tubular framework a distance of 20 millimeters or more.

9. A stent comprising:
a radially expandable tubular framework having a proximal end, a distal end, and a lumen extending therethrough, the tubular framework including a proximal end region extending to the proximal end of the tubular framework, a distal end region extending to the distal end of the tubular framework, and a cylindrical medial region extending between the proximal end region and the distal end region;
a covering surrounding the tubular framework, the covering being affixed to the tubular framework at a first affixment location and at a second affixment location, the first affixment location positioned proximate a junction between the distal end region and the medial region of the tubular framework, and the second affixment location positioned proximate a junction between the proximal end region and the medial region of the tubular framework;

the covering including a proximal region located proximal of the first affixment location and surrounding the medial region of the tubular framework;

the covering including a skirt located distal of the first affixment location and surrounding the distal end region of the tubular framework;

wherein the skirt is selectively removable from the distal end region of the tubular framework to expose the distal end region of the tubular framework; and a drawstring attached to the skirt, wherein the drawstring extends along the tubular framework to the proximal end of the tubular framework, wherein manipulation of the drawstring removes the skirt from the distal end region of the tubular framework.

10. The stent of claim 9, wherein a proximal end of the covering is located at the second affixment location such that the proximal end region of the tubular framework is devoid of the covering and is uncovered to permit hyperplastic tissue ingrowth through the proximal end region of the tubular framework.

11. The stent of claim 9, wherein the drawstring passes radially inward of the first and second affixment locations as the drawstring passes distally from the proximal end of the tubular framework to the skirt.

12. The stent of claim 11, wherein the drawstring extends along the medial region of the tubular framework between an inner surface of the proximal region of the covering and an outer surface of the tubular framework.

13. A stent delivery system comprising:

an elongate shaft having a handle at a proximal end thereof;

a radially expandable stent disposed on a distal region of the elongate shaft; the stent including:

a radially expandable tubular framework having a proximal end, a distal end, and a lumen extending therethrough; and a covering surrounding the tubular framework, the covering being affixed to the tubular framework at a first affixment location;

the covering including a proximal region extending proximal of the first affixment location and surrounding a medial region of the tubular framework;

the covering including a skirt extending distal of the first affixment location and surrounding a distal end region of the tubular framework;

wherein the skirt is selectively removable from the distal end region of the tubular framework to expose the distal end region of the tubular framework;

a drawstring extending from the skirt to the handle, wherein manipulation of the drawstring removes the skirt from the distal end region of the tubular framework.

14. The stent delivery system of claim 13, a thread surrounding the stent to constrain the stent in a radially contracted configuration on the distal region of the elongate shaft.

15. The stent delivery system of claim 13, wherein the drawstring loops through a grommet on the skirt.

16. The stent delivery system of claim 13, wherein the drawstring passes through an opening into a lumen of the elongate shaft proximal of the stent and extends through the lumen of the elongate shaft to the handle.

17. The stent delivery system of claim 13, wherein the skirt surrounds but is not directly affixed to the tubular framework distal of the first affixment location.

\* \* \* \* \*